United States Patent [19]

Campbell

[11] Patent Number: 5,184,046
[45] Date of Patent: Feb. 2, 1993

[54] CIRCULAR WAVEGUIDE PLASMA MICROWAVE STERILIZER APPARATUS

[75] Inventor: Bryant A. Campbell, Los Gatos, Calif.

[73] Assignee: Abtox, Inc., Pleasanton, Calif.

[21] Appl. No.: 589,511

[22] Filed: Sep. 28, 1990

[51] Int. Cl.$^5$ ............................ H05H 1/46; A61L 2/00
[52] U.S. Cl. ..................... 315/111.21; 313/231.31;
422/21; 422/22; 422/23; 250/455.11
[58] Field of Search ............. 315/111.21, 111.41;
313/231.31; 422/21, 22, 23; 250/455.1

[56] References Cited

U.S. PATENT DOCUMENTS

| | | |
|---|---|---|
| 3,383,163 | 5/1968 | Menashi ........................ 21/54 |
| 3,704,096 | 11/1972 | Verses et al. ................. 23/230 R |
| 3,737,608 | 6/1973 | Nagao et al. ................ 422/21 X |
| 3,851,436 | 12/1974 | Fraser et al. ................. 53/21 RC |
| 3,948,601 | 4/1976 | Fraser et al. ................... 422/23 |
| 4,169,123 | 9/1979 | Moore et al. .................. 422/29 |
| 4,169,124 | 9/1979 | Forstrom et al. ............... 422/33 |
| 4,207,286 | 6/1980 | Boucher ........................ 422/21 |
| 4,230,663 | 10/1980 | Forstrom et al. ............... 422/33 |
| 4,289,728 | 9/1981 | Peel et al. .................. 422/2 X |
| 4,321,232 | 3/1982 | Bithell .......................... 422/21 |
| 4,348,357 | 9/1982 | Bithell .......................... 422/22 |
| 4,366,125 | 12/1982 | Kodera et al. ................. 422/295 |
| 4,437,567 | 3/1984 | Jeng ........................... 206/210 |
| 4,643,876 | 2/1987 | Jacobs et al. .................. 422/23 |

FOREIGN PATENT DOCUMENTS 58-103460 6/1983 Japan .
58-162276 9/1983 Japan .

OTHER PUBLICATIONS

Goode et al., "A Review of Instrumentation Used to Generate Microwave-Induced Plasmas", *Applied Spectroscopy*, vol. 38, No. 6, 1984, pp. 755-763.
Rizzi, "Circular Waveguide", *Microwave Engineering Passive Circuits*, New Jersey: Prentice-Hall, pp. 216-217 (1988).
Veley, "Circular Waveguides", *Modern Microwave Technology*, New Jersey: Prentice-Hall, pp. 132-135 (1987).
Gandhi Om P., *Microwave Engineering and Applications*, New York: Pergamon Press, pp. 77, 98 (1981).

*Primary Examiner*—Eugene R. LaRoche
*Assistant Examiner*—Do Hyun Yoo
*Attorney, Agent, or Firm*—Majestic, Parsons, Siebert & Hsue

[57] ABSTRACT

An apparatus for plasma sterilization including a sterilization chamber and at least one microwave plasma generator for producing gas plasma products communicating therewith. The mircowave plasma generator includes a cylindrical metal waveguide and an axially concentric magnetron antenna extending into the waveguide. The plasma generator includes an inner plasma container made of a electromagnetic transparent material.

3 Claims, 4 Drawing Sheets

CIRCULAR WAVEGUIDE PLASMA MICROWAVE STERILIZER APPARATUS

FIELD OF THE INVENTION

This invention relates to an apparatus for sterilizing articles with a gas plasma generated from a mixture of oxygen; argon, helium and/or nitrogen; and hydrogen gases. In particular, this invention relates to a plasma sterilizing apparatus having a sterilizing chamber communicating with a plasma generator. The plasma generator is a cylindrical waveguide microwave plasma system including a magnetron antenna which injects the microwave energy field axially into a sealed coaxial gas containing an antechamber which is transparent to the microwave energy.

1. Background of the Invention

A variety of gas sterilization methods has been investigated in the past. Methods using ethylene oxide and other disinfecting gases are widely used for sterilizing a wide range of medical products from pharmaceutical preparations to surgical instruments. Irradiation alone and together with disinfecting gases has also been investigated, as summarized by Russell, A. THE DESTRUCTION OF BACTERIAL SPORES. New York: Academic Press (1982).

A sterilizing method must effectively kill all organisms, including spores, without damage to the article or goods being sterilized. However, many disinfecting gases which meet this criteria, such as ethylene oxide and irradiation methods, have been found to expose workers and the environment to unacceptable safety hazards. States and Federal legislation are severely restricting the amount of hazardous gases such as ethylene oxide (a carcinogen) in the working environment, or the use of any system or method which produces toxic residues or exhaust products. This is presenting a major crisis in hospitals and other areas of the health industry.

The use of plasma to sterilize containers was suggested in U.S. Pat. No. 3,383,163. Plasma is an ionized body of gas which may be generated by the application of power from different sources. The ionized gas will contact microorganisms on the surfaces of the items to be sterilized and effectively destroy the microorganisms.

Sterilizing plasmas have been generated with a wide variety of gases: argon, helium or xenon (U.S. Pat. No. 3,851,436); argon, nitrogen, oxygen, helium or xenon (U.S. Pat. No. 3,948,601); glutaraldehyde (U.S. Pat. No. 4,207,286); oxygen (U.S. Pat. No. 4,321,232); oxygen, nitrogen, helium, argon or freon with pulsed pressure (U.S. Pat. No. 4,348,357); hydrogen peroxide (U.S. Pat. No. 4,643,876); nitrous oxide, alone or mixed with oxygen, helium or argon (Japanese Application Disclosure No. 103460-1983); and nitrous oxide, alone or mixed with ozone (Japanese Application No. 162276-1983). Unfortunately, these plasma methods have proven to be too corrosive to articles being sterilized, and particular packaging materials; have left toxic residues on the sterilized articles; or have presented other safety or environmental hazards.

Non-plasma gas sterilization procedures have been described using ozone (U.S. Pat. No. 3,704,096) and hydrogen peroxide (U.S. Pat. Nos. 4,169,123, 4,169,124, 4,230,663, 4,366,125, 4,289,728, 4,437,567 and 4,643,876). These materials are toxic and leave undesirable residues.

2. Description of the Prior Art

Plasma gas sterilizer systems described in U.S. Pat. Nos. 3,851,436 and 3,948,601 have a plasma RF generation chamber and a separate sterilizing chamber. Products of a gas plasma produced in the chamber with argon, helium, nitrogen, oxygen or xenon are passed into a separate sterilization vacuum chamber. U.S. Pat. No. 4,643,876 describes a hydrogen peroxide plasma RF generation chamber which also functions as the sterilizing chamber. The articles being sterilized are exposed directly to electromagnetic radiation, damaging non-metallic components of the articles or packages being sterilized. Matching networks or equivalent adjusting means are required with RF systems to adjust the system to the conductivity variations in the electromagnetic field of the plasma generating zone introduced by metallic articles.

Goode, S. R. et al, Appl.Spectroscopy. 38:755-763 (1984) disclose a variety of microwave generating systems, including use of cylindrical cavity plasma systems with axial microwave generators. The TM operating modes and their advantages are also defined.

Rizzi, P. A., MICROWAVE ENGINEERING PASSIVE CIRCUITS. New Jersey: prentice-Hall, pp 216–217 (1988) discloses a cylindrical waveguide in $TM_{01}$ mode.

Veley, V. F., MODERN MICROWAVE TECHNOLOGY. New Jersey: Prentice-Hall, pp 132–135 (1987)—discloses a cylindrical waveguide in $TM_{01}$ mode.

SUMMARY AND OBJECTS OF THE INVENTION

The apparatus of this invention is an apparatus for plasma sterilization comprising a sterilization chamber and at least one microwave plasma generator for producing gas plasma products communicating therewith. The plasma generator comprises a cylindrical metal waveguide, and a magnetron antenna which injects the microwave energy field axially into a sealed coaxial gas containing an antechamber which is transparent to the microwave energy. One end of the waveguide is closed with a metal plate, and the antenna extends therethrough. The other end of the waveguide is closed with a metal plate having an outlet passageway for exit of plasma gas products, the outlet passageway and the waveguide having, for example, a common central axis. However, it is important to note, that according to the present invention, it is not necessary to have a common central axis, and plasma gas products can be brought out at any angle to the axis of the waveguide.

Preferably, the waveguide has an inner plasma container, preferably a concentric, cylindrical container, made of an electromagnetic transparent material such as quartz or TEFLON, the container having a gas inlet and a plasma product outlet conduit. It can have a distributor arrangement communicating with the plasma gas generator, for distributing plasma gas products in the sterilizing chamber. Optimally, the waveguide has an axial length L, corresponding to the formula:

$$L = (n)\frac{\lambda_g}{2}$$

wherein n is an integer, and $\lambda_g$ is the guide wavelength of the waveguide and is defined by the following:

$$\lambda_g = \frac{\lambda}{\sqrt{1 - \left(\frac{f_c}{f}\right)^2}}$$

wherein
$\lambda$ = wavelength
$f_c$ = cutoff frequency
f = operating frequency of the magnetron The diameter (D) of the waveguide is further defined by this relationship—$\lambda_c = 1.31$ D, $\lambda_c$ corresponding to the cutoff wavelength.

A plasma is, by definition, a partially ionized gas containing molecules, atoms, ions, electrons and free radicals. At lower pressures, it has been determined that electron temperatures are typically many times greater than the temperatures of free radicals and of the gas itself. This nonequilibrium plasma system is defined as a cold plasma. The cold plasma is further defined as having a high E/P ratio, where E is the electric field strength and P is the pressure. Circular wave guides operating in the Tmol mode generate electric field strengths which are greater in magnitude than the traditional rectangular waveguide methods of coupling microwave energy into a plasma antechamber, and therefore, is the preferred method of implementation for the generation of the maximum number of free radicals at the lowest possible temperature.

It is an object of this invention to provide a plasma sterilizer which operates at low temperatures, low gas consumption and effectively sterilizes all types of articles, packaged or unpackaged, without damaging the article or packaging.

It is a further object of this invention to provide a plasma sterilizer which provides sterilizing gaseous plasma products which can be used alone or in conjunction with ancillary treatment of articles with vaporized antimicrobial chemicals to provide complete killing of spores.

DETAILED DESCRIPTION OF THE INVENTION

Figure 1:
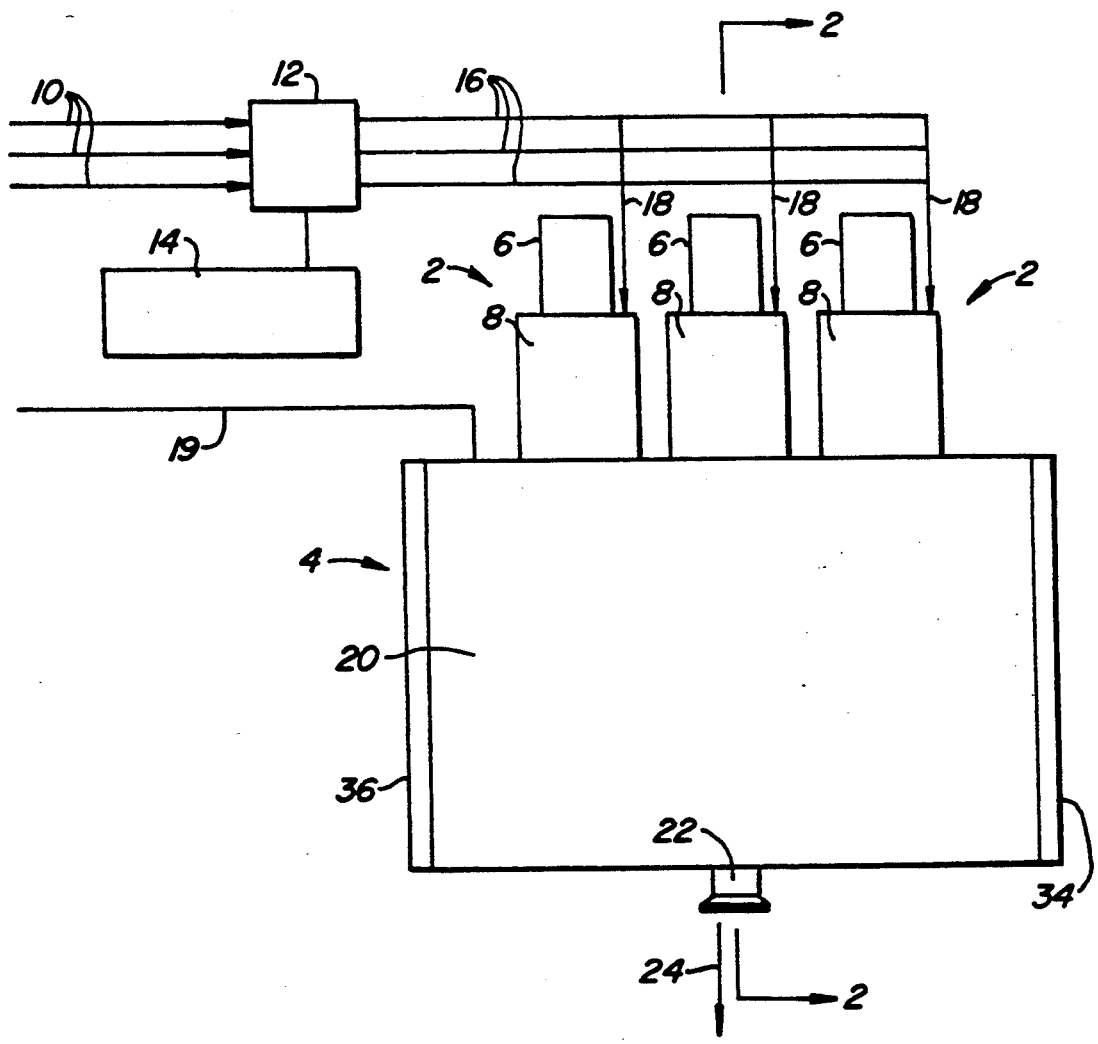
FIG. 1 is a front view of the plasma sterilizer of this invention.

Hospitals originally relied on disinfectants and steam autoclaves for sterilizing implements. In more recent years, ethylene oxide gas sterilization has made possible the sterilization of packaged articles, drugs and medical supplies, and hospital systems are highly dependent upon these procedures. Ethylene oxide is now known to be a dangerous carcinogen, however, and a number of new state laws protecting worker safety and the environment are precluding or greatly restricting further use of ethylene oxide sterilizers in hospital environments.

Numerous gas plasma sterilizers using a wide variety of gases have been described in the patent literature. A few have been commercially produced, and a few have focused on residue contamination problems. The previously described gas sterilizers either fail to satisfy current regulatory residue and exhaust emission safety standards of several states, because they either leave unacceptable residues or produce exhaust emissions which are potentially hazardous to hospital personnel, or they cause unacceptable destruction of packaging materials. They are thus not satisfactory for replacing ethylene oxide sterilizers.

The gas sterilizer of this invention produces a plasma from gas mixtures containing argon, helium and/or nitrogen; and oxygen and/or hydrogen; and optional inert gases and carbon dioxide. The exhaust gas products fully satisfy current environmental and worker safety concerns, the products of the plasma being almost entirely water vapor, carbon dioxide and nontoxic gases normally found in the atmosphere.

The term "plasma" as used herein is defined to include any portion of the gas or vapors which contain electrons, ions, free radicals, dissociated and/or excited atoms or molecules produced as a result of an applied electric or electromagnetic field including any accompanying radiation which might be produced. The electromagnetic field can cover a broad frequency range, and is produced by various frequency generators.

One embodiment of a plasma sterilizing apparatus having a separate plasma generator and sterilizing chamber is described in commonly assigned, copending application Ser. No. 07/576,292 filed Aug. 31, 1990, now U.S. Pat. No. 5,115,166 issued May 19, 1992, the entire contents of which are hereby incorporated by reference. In that embodiment, the plasma is generated in a rectangular waveguide. However, maintaining the process gas pressure in the generator higher than the sterilizer vacuum chamber pressure was found to be necessary to obtain and retain a stable plasma in the plasma generating chamber, and this required the presence of a restriction in the generator outlet passageway. With some gases, the use of a secondary energy source such as a spark was found to be necessary to initiate the plasma. In contrast, with the cylindrical waveguide plasma generator in the sterilizer of this invention, the plasma can be reliably initiated and maintained at process gas pressures approximating the sterilizing chamber vacuum pressure without the use of a secondary energy source.

FIG. 1 is a front view of the plasma sterilizer of this invention. The plasma sterilizer comprises one or more plasma generators 2 and a sterilizing cabinet 4. The plasma generators includes magnetron electromagnetic field generators 6 and cylindrical waveguides 8 which can be supported on the sterilizing cabinet 4.

The plasma source gases are fed through process gas supply tubes 10 to a control valve complex 12. The operation of the control valves is controlled by standard procedures with a conventional central processing unit (CPU) 14 connected therewith. The gas flows providing the precise process gas mixture desired are thus regulated. The process gases are directed by supply tubes 16 to the plasma chamber inlet conduits 18 where they mix to form the desired process gas compositions. Addition treatment fluids can be introduced directly into the sterilizing cabinet by secondary treatment fluid conduit 19.

The sterilizing cabinet has a door 20 and a exhaust gas outlet port 22 connected to a conventional exhaust vacuum system (not shown), through which exhaust gases 24 are removed. With a suitable selection of process gases, the exhaust gases are environmentally safe and non-toxic.

Figure 2:
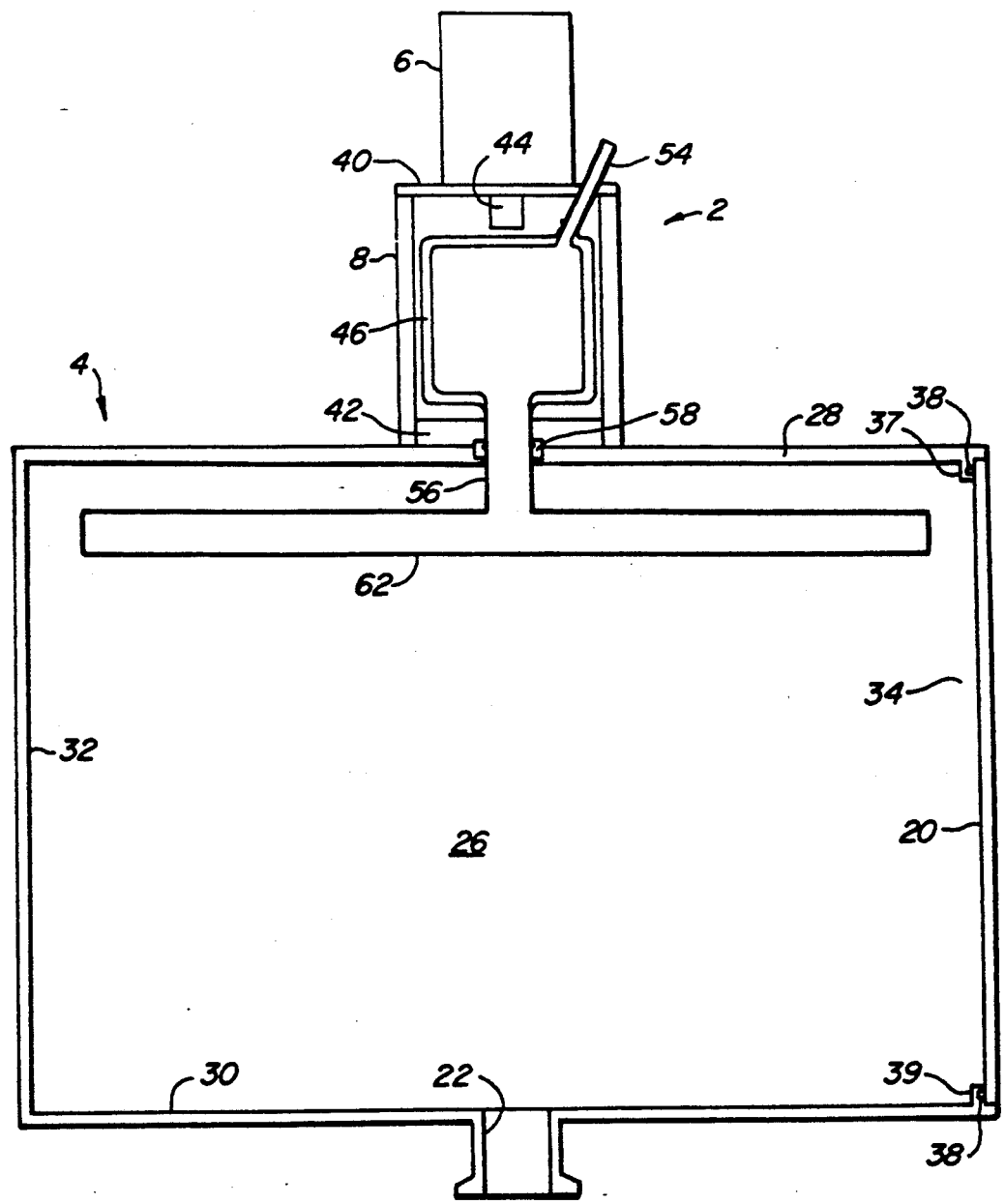
FIG. 2 is a cross-sectional view of the plasma sterilizer of FIG. 1, taken along the line 2—2 of FIG. 1.

FIG. 2 is a cross-sectional view of the plasma sterilizer of FIG. 1, taken along the line A—A of FIG. 1. The sterilizing cabinet 4 comprises a sterilizing chamber 26 defined by metallic ceiling and floor plates 28 and 30, backplate plate 32, door 20, and end plates 34 and 36 (FIG. 1). The door 20 is secured in a sealed relationship with the sterilizing chamber. It is hinged at the top, side or bottom with conventional hinge pins (not shown) to swing against abutting surfaces 37 and 39, and an O-ring seal 38.

Figure 3:
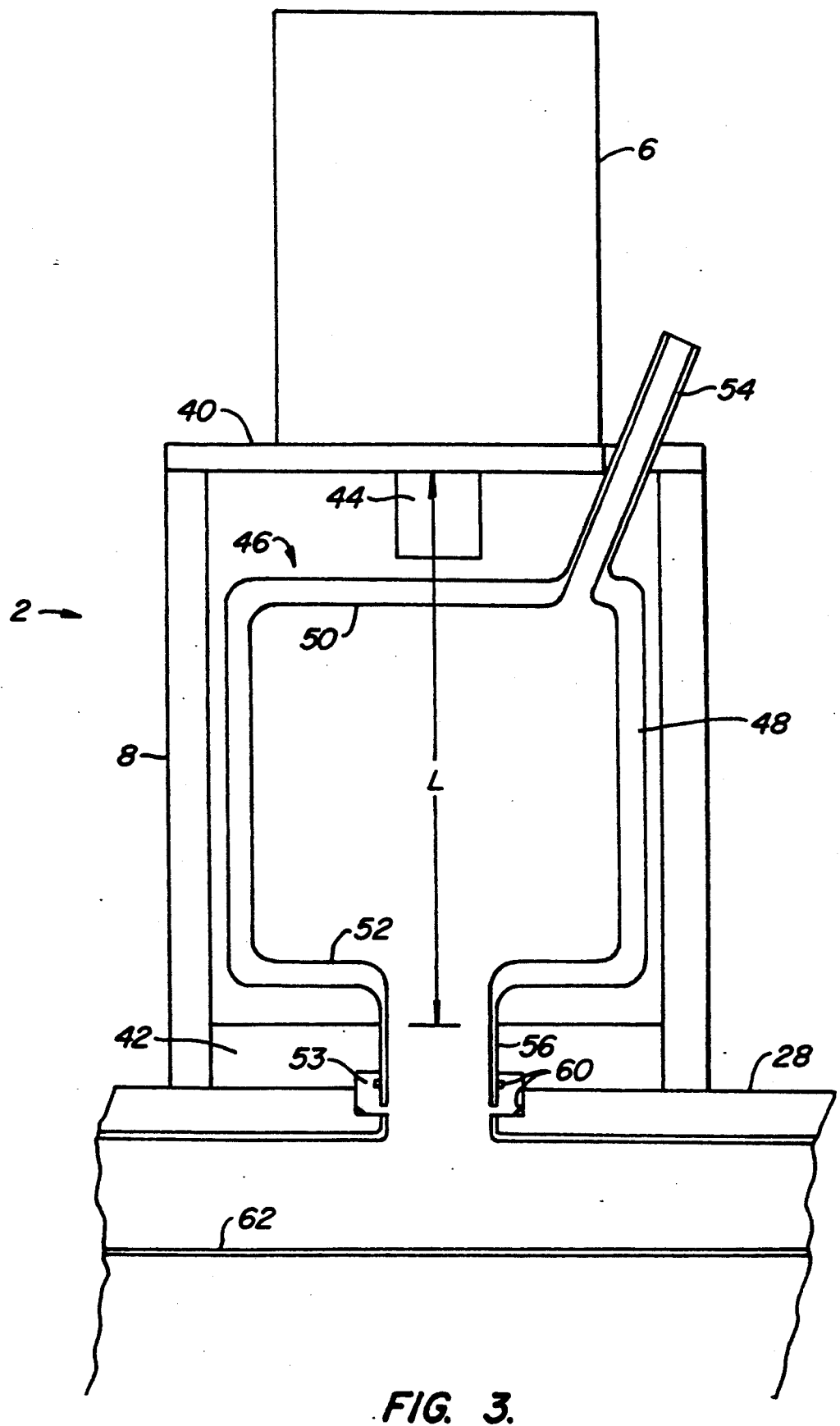
FIG. 3 is a detailed, fragmentary cross-sectional view of the cylindrical microwave plasma generator of this invention.

FIG. 3 is a detailed, fragmentary cross-sectional view of the cylindrical microwave plasma generator of this invention. The plasma generator 2 comprises the metallic cylinder 8, metallic magnetron and antenna support plate 40 and metallic shorting floor plate 42. The magnetron antenna 44 is axially concentric with the cylinder 8. The plasma is generated in the cylindrical plasma container 46 made of a material which is transparent to electromagnetic radiation and has the strength to withstand reduced pressure when evacuated. A suitable material is quartz or pyrex, for example. The plasma container 46 is essentially a bottle with a cylindrical sidewall 48 and integral top and bottom ends 50 and 52. It has an integral process gas inlet conduit 54 for introducing a flow of process gases into the interior of the container where the plasma is produced. It also has an integral plasma outlet conduit 56 through which gaseous plasma products are fed to distributor 62 and into the sterilizing chamber. The plasma container outlet conduit 56 passes into the sterilizing chamber through sealing ring 58. Sealing ring 58 has two 0-ring seals 60 which form a seal between the outer surface of the conduit 56 and the top plate 28 of the sterilizing cabinet. The plasma outlet conduit 56 leads to plasma distributor 62. The plasma distributor has holes (not shown) in the lower surface to distribute gaseous plasma products across the full width of the sterilizing cabinet. The plasma products flow downward over objects to be sterilized and are exhausted through outlet port 22.

The cylindrical waveguide magnetron plasma generator produces plasmas more efficiently with less power and lower gas consumption than rectangular waveguide configurations with rf generator systems. It allows operation independent of power and flow within a given band. The cylindrical waveguide is preferably operated in the $TM_{01}$ mode described by Rizzi and Veley (supra) because of the increased energy coupling into the gas which satisfies the equation E/P as mentioned previously. In this mode, the magnetron couples into the waveguide axially, not from the side.

Electromagnetic field frequencies within the range of from about 915 MHz to $10^6$ MHz can be easily generated by conventional magnetron microwave generators. Preferred frequencies are within the range of from about 915 MHz to 2450 MHz because of cost, FCC regulations and waveguide sizing considerations. Magnetrons that operate at 2.45 GHz are the most practical due to their use in the commercial heating marketplace where the large volume has brought the price down.

To insure propagation of the $TM_{01}$ mode only, the upper frequency limit of the magnetron is preferably set five percent below the cutoff frequency of the $TM_{11}$ mode. The lower frequency is preferably set to approximately twenty-five percent above the cutoff frequency of the $TM_{01}$ mode.

Figure 4A:
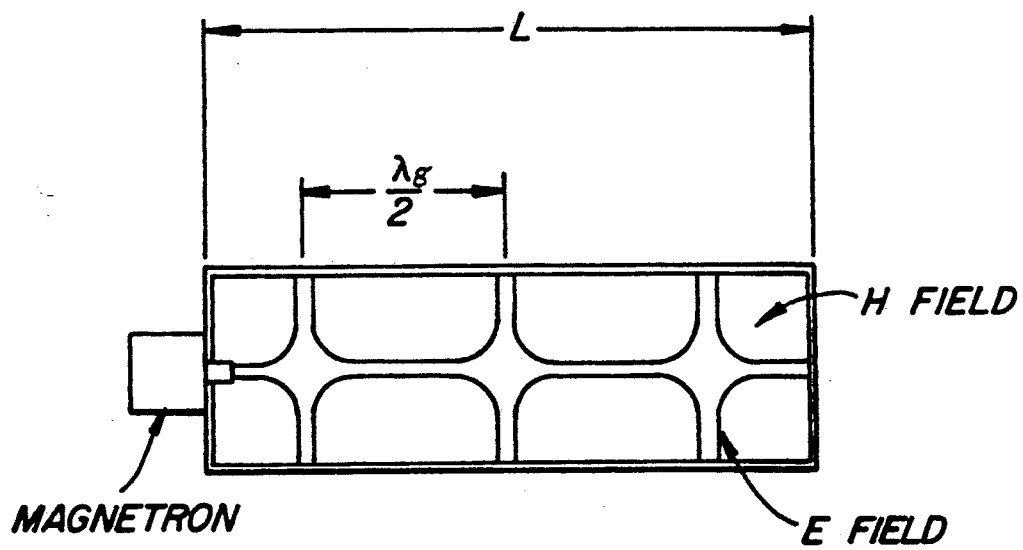
FIGS. 4A-4B are respectively detailed, cross-sectional side and end views of the electro (E) and magnetic (H) field for a Tmol wave propagation for a circular waveguide.
Figure 4B:
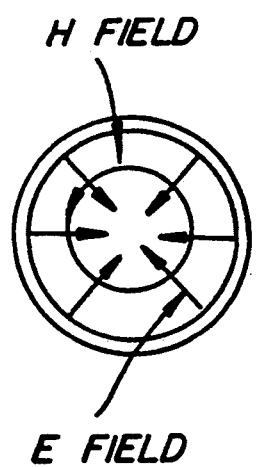

The axial length of the cylindrical waveguide, L, is the distance between the antenna support plate 40 of the antenna 44 and the shorting end plate 42. The waveguide length, L, is selected based on increments of $\lambda_g/2$ as shown in FIG. 4. Therefore, the guide wavelength ($\lambda_g$) can be determined by the formula:

$$\lambda_g = \frac{\lambda}{\sqrt{1-\left(\frac{f_c}{f}\right)^2}}$$

wherein $\lambda_g$ is the guide wavelength of the magnetron, which is further defined by the operating frequency of the magnetron, i.e.

$$\lambda = \frac{30}{f}, \text{ and}$$

where:
$\lambda$ = wavelength (cm)
$f$ = frequency (GHz)
$f_c$ = cutoff frequency (GHz).

The apparatus of this invention can be used to generate a sterilizing plasma from a mixture of oxygen; argon, helium, and/or nitrogen; and hydrogen, or with a mixture of air and hydrogen, supplemented by oxygen or nitrogen to give the desired ratios. The sterilization is carried out at a vacuum pressure of from 0.1 to 10 torr and preferably from 1 to 3 torr. The temperature in the sterilizing chamber is maintained below 63° C. and preferably from 38° to 54° C. Under these conditions, effective sterilization is effected without significant deterioration of packaging materials in which articles to be sterilized may be placed.

The method for plasma sterilization comprises exposing an article to be sterilized to a plasma generated from a gaseous mixture of argon, helium or nitrogen mixed with oxygen and/or hydrogen at temperatures of less than 63° C., a pressure of from 0.1 to 10 torr, and a treatment time of at least 5, and preferably from 10 to 15 minutes. For sterilizing packaged goods, the gas mixtures from which the plasma is generated can contain from 1 to 21 (v/v) % oxygen and from 1 to 20 (v/v) % hydrogen, the balance being argon, helium and/or nitrogen and optional small quantities of inert gases.

The gas mixtures producing plasmas for sterilizing packages preferably contain from 1 to 10 (v/v) % oxygen and from 2 to 8 (v/v) % hydrogen, and optimally contain from 2 to 8 (v/v) % oxygen and from 3 to 7 (v/v) % hydrogen. Packages are treated for at least 15 minutes and preferably from 1 to 5 hours.

In an alternate embodiment, packaged goods are sterilized by treatment for at least 15 minutes and preferably from 1 to 5 hours with plasma generated from a gas mixture containing from 1 to 10 (v/v) % hydrogen and from 90 to 99 (v/v) % argon, helium and/or nitrogen, with little or no amounts of oxygen being present, the optimum mixture comprising 5 (v/v) % hydrogen and about 95 (v/v) % argon.

Contaminated goods may require a deproteinizing step prior to the sterilization step. Plasma deproteinizing can be effected by treating the objects to be sterilized at temperatures of less than 63° C. and pressures of from 1 to 10 torr with plasma generated from a gas mixture of from 90 to 100 (v/v) % oxygen, from 0 to 10 (v/v) % argon and optional amounts of hydrogen. Deproteinizing is effected by treating the contaminated articles with plasmas generated from these gas mixtures for at least 1 minute and preferably for from 1 to 5 minutes. Because of the harshness of the plasma produced by this plasma composition, exposure of packaged goods should be limited to the time effective to remove the original contaminating substances.

Objects which are resistant to oxidation such as metallic surgical instruments can be sterilized by treatment for at least 1 minute and preferably for at least 5 minutes with plasma generated from a gas mixture containing from 10 to 40 (v/v) % oxygen; from 60 to 90 (v/v) % argon, helium and/or nitrogen; and optional amounts of hydrogen and/or inert gases at a temperature of preferably less than 63° C. and a pressure of from 1 to 10 torr. The plasma can be generated from air (21 v/v % oxygen, 78 v/v % nitrogen, etc.), for example.

A residence time of from 5 to 10 minutes is usually sufficient to sterilize most articles. Clean articles packaged in envelopes or other shapes having porous surfaces allowing easy penetration of the plasma are usually completely sterilized within 60 minutes.

In an optimum method of sterilizing, the articles to be sterilized are placed in the sterilizing chamber, supported by conventional grids which permit the plasma to reach all surfaces of the articles. The chamber is closed, the sterilizing chamber is evacuated, plasma generation is begun, and the plasma is directed into and through the sterilizing chamber.

The plasma components have a short life, and quickly decay to form water vapor (gas), carbon dioxide, and other non-toxic components usually found in air. These are fully acceptable as residues or as exhaust gas components.

The cylindrical waveguide plasma sterilizer of this invention can be used with peracetic acid and/or hydrogen peroxide treatments of the articles such as are the subject of copending, commonly assigned applications Ser. No. 07/576,236 filed Aug. 31, 1990, now abandoned and Ser. No. 07/576,231 filed Aug. 31, 1990, now abandoned.

I claim:

1. An apparatus for plasma sterilization comprising:
   a sterilization chamber;
   a plasma container made of a material transparent to an electromagnetic radiation, said plasma container having a gas inlet for admitting a plasma generation gas and a plasma product outlet conduit for passing plasma gas products into said sterilization chamber;
   at least one microwave plasma generator for producing plasma gas products in said plasma container, said microwave plasma generator further comprising:
   a magnetron for generating electromagnetic radiation,
   a cylindrical metal waveguide enclosing said plasma container for guiding the electromagnetic radiation thereto, and
   an axially concentric magnetron antenna extending into the cylindrical waveguide for feeding the electromagnetic radiation from the magnetron to the cylindrical waveguide.

2. An apparatus of claim 1 wherein the plasma container is made of quartz.

3. An apparatus of claim 1 wherein the plasma container is concentric with the waveguide.

* * * * *